(12) United States Patent
Zhang et al.

(10) Patent No.: US 8,184,890 B2
(45) Date of Patent: May 22, 2012

(54) COMPUTER-AIDED DIAGNOSIS AND VISUALIZATION OF TOMOSYNTHESIS MAMMOGRAPHY DATA

(75) Inventors: Heidi Daoxian Zhang, Los Gatos, CA (US); Patrick Bernard Heffernan, Los Gatos, CA (US)

(73) Assignee: Three Palm Software, Los Gatos, CA (US)

( * ) Notice: Subject to any disclaimer, the term of this patent is extended or adjusted under 35 U.S.C. 154(b) by 561 days.

(21) Appl. No.: 12/344,451

(22) Filed: Dec. 26, 2008

(65) Prior Publication Data

US 2010/0166267 A1 Jul. 1, 2010

(51) Int. Cl.
*G06K 9/00* (2006.01)
(52) U.S. Cl. .......................... 382/131; 382/128; 128/922
(58) Field of Classification Search .......... 382/128–134; 128/922
See application file for complete search history.

(56) References Cited

U.S. PATENT DOCUMENTS

| | | | |
|---|---|---|---|
| 6,375,352 B1 | 4/2002 | Hewes et al. | |
| 6,707,878 B2 | 3/2004 | Claus et al. | |
| 6,748,044 B2 | 6/2004 | Sabol et al. | |
| 7,127,029 B2 | 10/2006 | Francke | |
| 2003/0007598 A1* | 1/2003 | Wang et al. | ...................... 378/37 |
| 2004/0184647 A1* | 9/2004 | Reeves et al. | ................. 382/131 |
| 2006/0177125 A1 | 8/2006 | Chan et al. | |

* cited by examiner

*Primary Examiner* — David Mis
(74) *Attorney, Agent, or Firm* — Haynes and Boone, LLP

(57) ABSTRACT

The present invention provides a method and system using computer-aided detection (CAD) algorithms to aid diagnosis and visualization of tomosynthesis mammography data. The proposed CAD algorithms process two-dimensional and three-dimensional tomosynthesis mammography images and identify regions of interest in breasts. The CAD algorithms include the steps of preprocessing; candidate detection of potential regions of interest; and classification of each region of interest to aid reading by radiologists. The detection of potential regions of interest utilizes two dimensional projection images for generating candidates. The resultant candidates in two dimensional images are back-projected into the three dimensional volume images. The feature extraction for classification operates in the three dimensional image in the neighborhood of the back-projected candidate location. The forward-projection and back-projection algorithms are used for visualization of the tomosynthesis mammography data in a fashion of synchronized MPR and VR.

15 Claims, 4 Drawing Sheets

COMPUTER-AIDED DIAGNOSIS AND VISUALIZATION OF TOMOSYNTHESIS MAMMOGRAPHY DATA

TECHNICAL FIELD

The present invention relates generally to medical imaging procedures. Particularly, the present invention relates to the utilization of computer-aided detection and diagnosis (CAD) algorithms and visualization techniques in conjunction with tomosynthesis mammography.

BACKGROUND

A tomosynthesis system may be used to form a three-dimensional (3-D) image of an object from a series of two-dimensional (2-D) images. The 2-D images may be obtained from a variety of sources including X-ray systems as used in medical applications. A series of 2-D X-rays of an area of interest of a patient may be used to reconstruct a 3-D image of that area of interest. The series of 2-D images, projection images, generated by the X-ray machine and/or the 3-D reconstruction image of the object are considered to be tomosynthesis data. A tomosynthesis system may be used to produce tomosynthesis data from mammography X-rays.

Compared to conventional 2-D X-ray mammography, tomosynthesis mammography generates a much larger amount data for radiologists to read. Therefore, it is desirable to develop computer-aided detection and diagnosis (CAD) algorithms and visualization techniques to assist radiologists in interpreting tomosynthesis mammography studies.

BRIEF SUMMARY OF THE INVENTION

Computer-aided detection and diagnosis (CAD) algorithms applied to mammography images may be basically comprised of three steps: (1) preprocessing to remove artifacts in images and segment the breast tissue area for later processing; (2) identifying potential regions of interest, such as, abnormal density areas in breast, or clusters of bright microcalcification spots; and (3) extracting features of the identified regions in order to produce classification information, such as, probability of cancer or benign findings.

Traditional CAD algorithms perform image processing either in two-dimensional (2-D) mammography projection images, or in three-dimensional (3-D) reconstructed volume images alone. Embodiments of the invention allow combining 2-D and 3-D image processing methods to visualize tomosynthesis mammography data and to identify and analyze the regions of interest in patient breast objects. The detection of potential regions of interest utilizes 2-D projection images for generating candidates. The resultant candidates detected in the 2-D images are back-projected to the 3-D volume data. Feature extraction for classification operates in the 3-D image in the neighborhood of the back-projected candidate location.

The potential regions of interest may be displayed in the 3-D volume data and/or the 2-D projection images. Visualization of an entire data set may be enabled using multiplanar reformatting (MPR) of the volume data in one of three fixed directions, or in an arbitrary direction as indicated by the user. Visualization of a region of interest may use volume rendering (VR) to produce the region in 3-D. Multiple sets of data may be produced from a single examination, including multiple mammographic views such as mediolateral oblique and craniocaudal views of the right and left breasts. Multiple sets of data may be viewed by using "synchronized" MPR and VR amongst the multiple data sets. Visualization of multiple sets of data from multiple examinations separated by time, such as a current mammography exam compared to a prior mammography exam, may use "synchronized" MPR and VR as well to facilitate comparison amongst the multiple examinations.

Consistent with some embodiments of the invention, there is provided herein a method using computer-aided detection (CAD) algorithms to aid diagnosis and visualization of tomosynthesis mammography data comprising processing tomosynthesis data with a CAD algorithm engine and visualizing tomosynthesis data in a user-selected direction. The user-selected direction is selected in a user interface from a plurality of visualization directions including directions corresponding to standard mammography views and directions that do not correspond to standard mammography views.

Additional embodiments provide a system using computer-aided detection (CAD) algorithms to aid diagnosis and visualization of tomosynthesis mammography data. Certain embodiments of the system comprise a CAD algorithm engine to process a set of tomosynthesis data, the set of tomosynthesis data comprising two-dimensional images and three-dimensional image data; and a user interface to visualize the set of tomosynthesis data in a user-selected direction selected from a plurality of visualization directions including directions corresponding to standard mammography views and directions not corresponding to standard mammography views using multiplanar reformatting and volume rendering.

DETAILED DESCRIPTION

Figure 1:
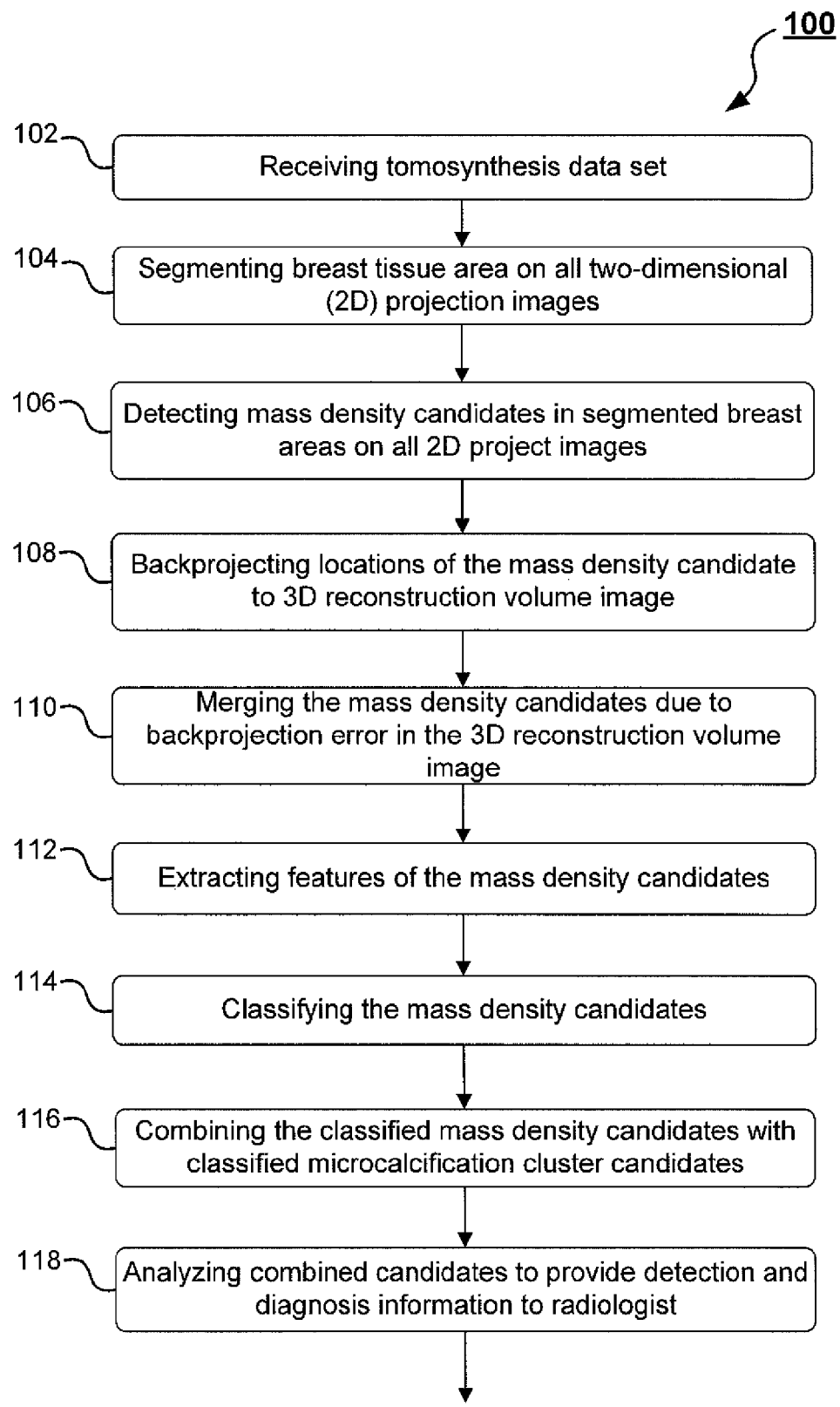
FIG. 1 depicts a flowchart of a method for using mass density data in 2-D and 3-D form to aid in diagnosis.

FIG. 1 depicts a method 100 performed by a CAD system for processing tomosynthesis data in order to facilitate diagnosis in a mammography context. Method 100 may begin in step 102 when the CAD system receives at least one tomosynthesis data set. The tomosynthesis data set may include a series of two-dimensional (2-D) mammography images of the same subject obtained from a variety of angles. The tomosynthesis data set may also include a 3-D reconstruction image produced using the series of 2-D mammography images. Thus, at step 102, the received data set may include a 3-D reconstruction image volume and the series of 2-D images, called projection images herein, used to produce it. Method 100 may continue in step 104 when the CAD systems segments the breast tissue area on all of the projection images. This may be accomplished by first finding the skin line in order to segment the breast tissue area from the background area in the projection images. All subsequent steps of method 100 may be performed inside the segmented breast tissue.

In step 106, the method 100 may continue when the CAD system detects mass density candidates from all of the projection images. Next, in step 108, the locations of the detected mass density candidates are back-projected into the 3-D reconstruction image volume using the same reconstructing filter. Due to the limited range of angles represented in the projection images, back-projection errors may introduce "ghost" candidates. The ghost candidates may be merged or removed, in step 110, using similarity or dissimilarity criteria from the candidates in the series of projection images. The 3-D features around the candidates' locations are extracted, in step 112, from the 3-D reconstruction image data. In step 114, the 3-D features are used to train and classify the candidates. The extracted 3-D features may include typical features that radiologists use to interpret 2-D mammograms, such as shape, margin, density, and distribution. All these features are calculated in 3-D using data from the 3-D reconstruction image in the vicinities of the detected mass density candidate locations.

In step 116, the CAD system may combine the mass density candidates classified as indicate above with classified microcalcification cluster candidates. The combined mass density and microcalcification cluster candidates may be analyzed, in step 118, to provide detection and diagnosis information to a radiologist using a mammography visualization workstation. The mass density candidates and microcalcification candidates may be combined to process and generate diagnosis information such as a probability of malignancy.

Figure 2:
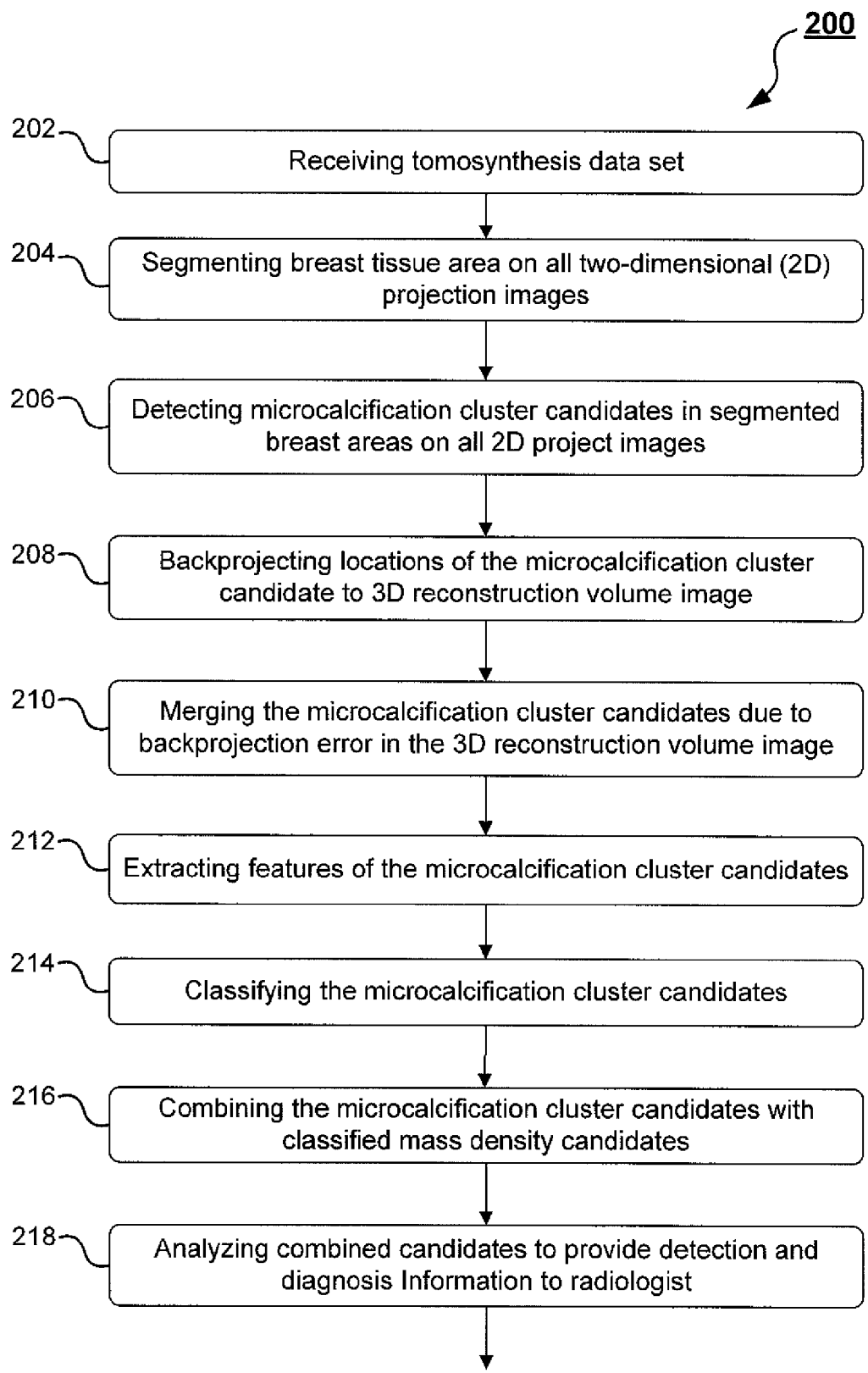
FIG. 2 depicts a flowchart of a method for using microcalcification cluster data in 2-D and 3-D form to aid in diagnosis.

FIG. 2 depicts a method 200 for processing tomosynthesis data in order to facilitate diagnosis in a mammography context. Some of the steps of method 200 may be similar to some of the steps of method 100. In step 202 a tomosynthesis data set may be received by a CAD system. The tomosynthesis data set may include a 3-D reconstruction image and the corresponding series of projection images. The breast tissue area on all of the projection images may be segmented in step 204. In step 206, the method 200 may continue when the CAD system detects microcalcification cluster candidates in all of the projection images. Next, in step 208, the locations of the detected microcalcification cluster candidates may be back-projected into the 3-D reconstruction image using the same reconstructing filter.

Ghost candidates may be merged or removed, in step 210, using similarity or dissimilarity criteria from the candidates in the series of projection images. The 3-D features around the candidates' locations may be extracted, in step 212, from the 3-D reconstruction image data. In step 214, the extracted 3-D features are used to train and classify the candidates. In step 216, the CAD system combine the microcalcification cluster candidates classified as indicated above with classified mass density candidates, which may be analyzed, in step 218, to provide detection and diagnosis information to a radiologist using a mammography visualization workstation.

Figure 3:
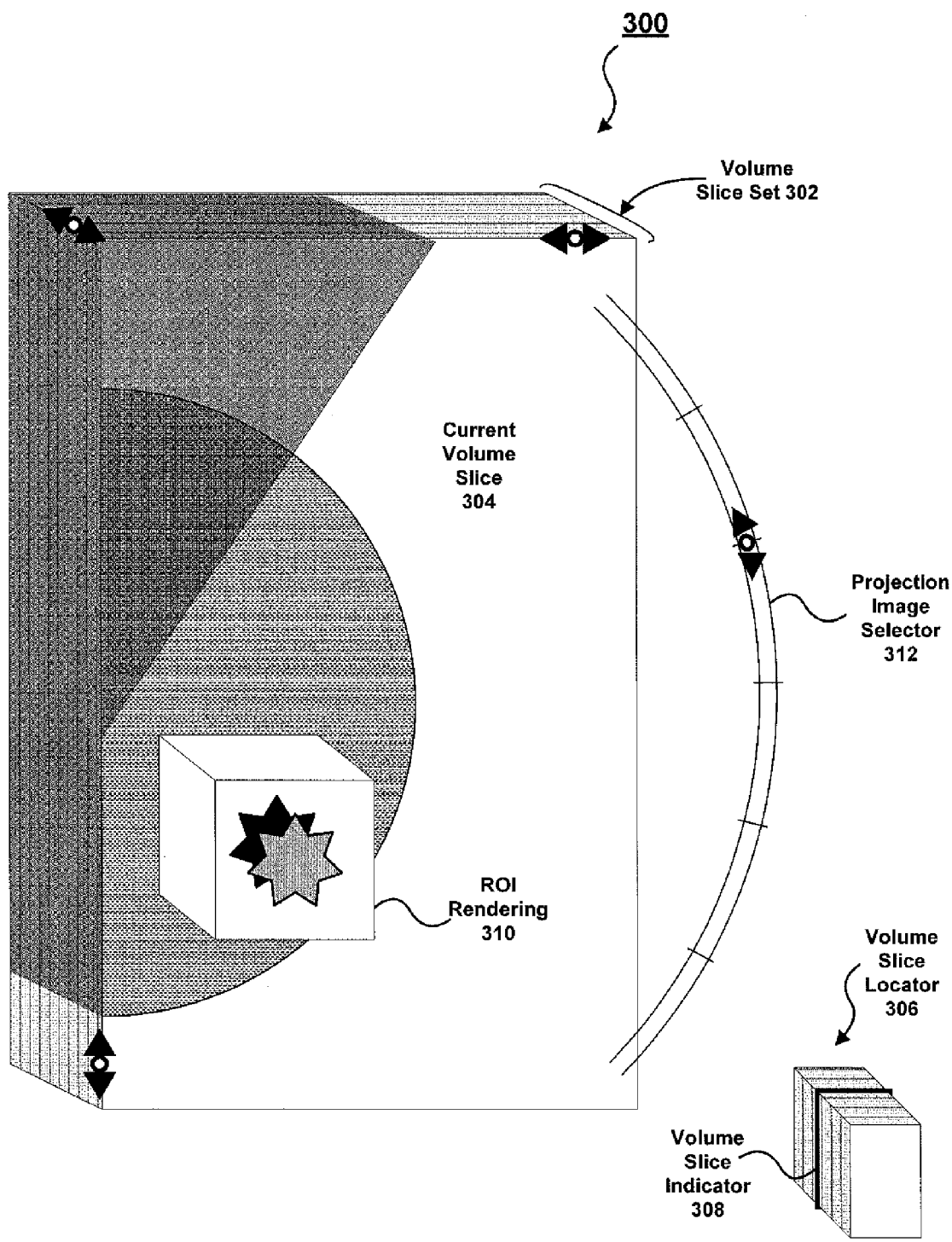
FIG. 3 shows a user interface system for visualization and manipulation of tomosynthesis data from a single data set.

FIG. 3 depicts a user interface 300 for visualization and manipulation of tomosynthesis data and additional data obtained from methods 100 or 200 running on a CAD system. The information processed by methods 100 or 200 may be used for visualization of the complete set of tomosynthesis data or specific regions of interest, either identified by the radiologist or detected by CAD. User interface 300 may comprise a volume slice set 302. Volume slice set 302 may be a series of multiplanar reformatted images obtained from a volume of 3-D reconstruction image data. The volume may be visualized in different directions, creating volume slice sets, such as volume slice set 302, in corresponding directions. A current volume slice 304, which is a 2-D image produced from the volume of 3-D reconstruction data, may be displayed for a user. User interface 300 may allow selection of any 2-D image in the volume slice set 302 to be displayed as current volume slice 304. This may be achieved by using a mouse-type scroll-wheel to scroll through each slice along a direction defined and selected by the user-radiologist.

A cube icon, volume slice locator 306, and an intersecting plane, volume slice indicator 308, may be used to indicate the location and orientation of the current volume slice 304 in the volume of 3-D reconstruction data. By using a pointer-type interfacing device to interact with the volume slice locator 306, a user may select a viewing angle from which to view the volume of 3-D reconstruction data. The pointer-type interfacing device may be a device such as a computer mouse. By selecting a side of the volume slice locator 306 cube, the user may cause the volume of 3-D data to be sliced parallel to the selected side, so that volume slice set 302 and current volume slice 304 have an orientation corresponding to the selected side. The volume slice locator 306 may also be used to select an arbitrary viewing direction, a direction not parallel to any side of depicted in volume slice locator 306, causing the volume of 3-D data to be slices in accordance with the viewing direction.

An "angle" icon, projection image selector 312, may be used to scroll through each original 2-D projection image. Scrolling may be accomplished by an interface manipulating device such as a mouse-type device with a scroll wheel. This may be desirable since the original projection images usually provide higher resolution or better 2-D image quality.

When a sub-region, or region of interest (ROI), is identified by the user-radiologist, a localized 3-D volume rendering, ROI rendering 310, may be used to visualize and analyze the region of interest on the 2-D current volume slice 304 in three dimensions. The interface 300 may allow a user to use a pointer, such as a mouse-type input, to select the region of interest for volume rendering. Thus, using the CAD forward- and back-projection information, the corresponding region of interest on 2-D projection images can be correlated and displayed on the same screen with its 3-D volume rendered image. A pointer device and scrolling device, such as may be found on a computer mouse, may be used to manipulate the volume to control the viewing angle and to cause volume rendering of regions of interest.

Figure 4:
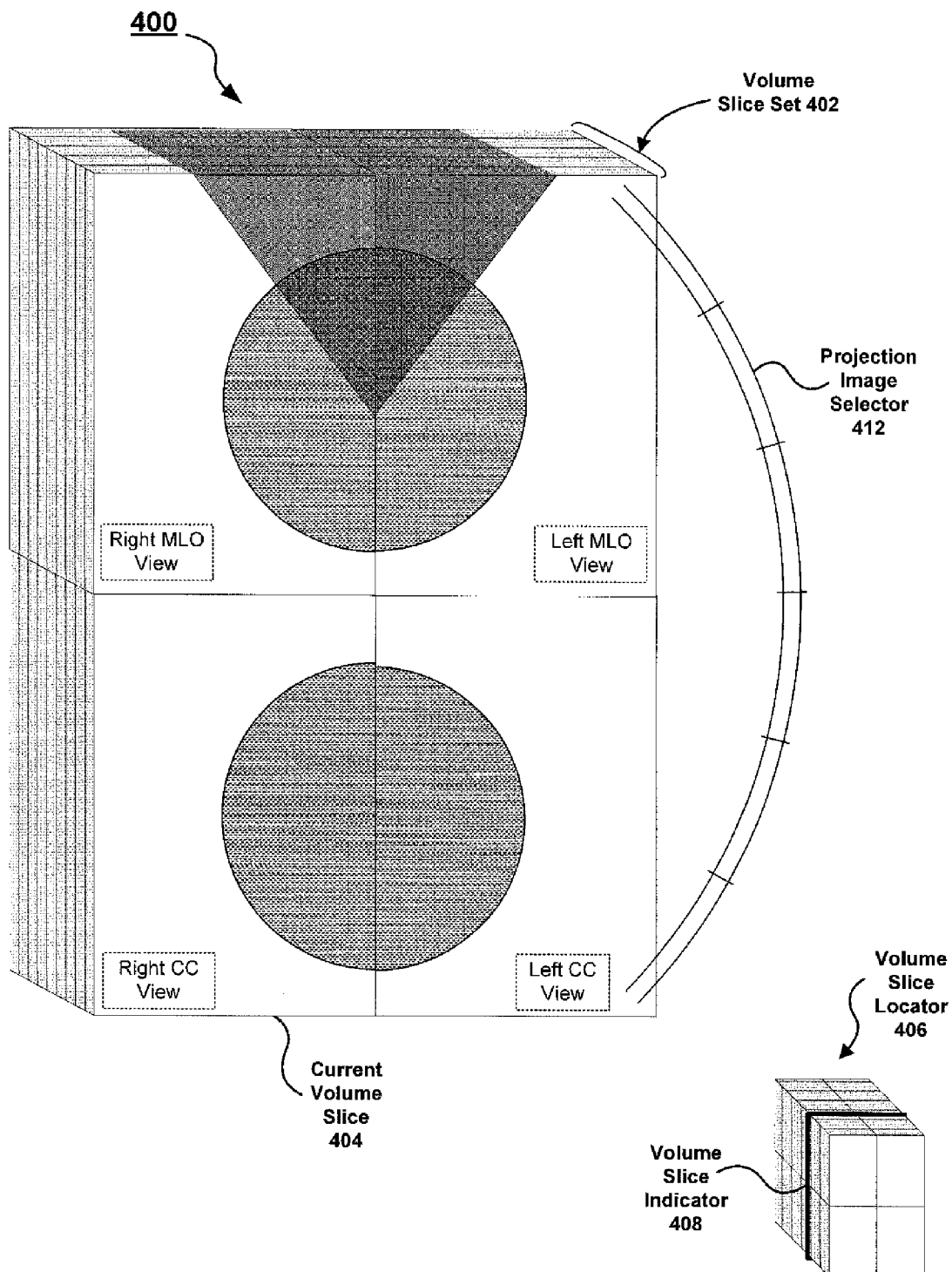
FIG. 4 shows a user interface system for visualization and manipulation of tomosynthesis data from multiple data sets.

FIG. 4 depicts a user interface 400 which may facilitate viewing multiple tomosynthesis data sets simultaneously. A typical screening mammography exam includes four acquisitions. There may be one acquisition for each of the left and right breasts acquired in two views: the craniocaudal (CC) view and the mediolateral oblique (MLO) view. Interpreting four acquisitions may usually involve bilateral comparison between right and left CC views or right and left MLO views in a synchronized style, or hanging protocol. Interpreting screening mammograms may also involve comparison with prior exams. Thus the visualization of multiple volumes of 3-D reconstructed data and multiple sets of 2-D projection images may need to be synchronized, as is shown in FIG. 4.

FIG. 4 contains a volume slice set 402, which may be similar to volume slice set 302. However, volume slice set 402 may include multiple tomosynthesis data sets. The multiple tomosynthesis data sets may include multiple views, including right and left MLO and CC views. Each view may comprise a corresponding tomosynthesis data set as labeled in FIG. 4. Thus a current volume slice 404 may comprise multiple current volume slices, one from each data set. Volume slice locator 406 reflects the multiple data sets in a volumetric form. Volume slice indicator 408 indicates to a user-radiologist where the 2-D current volume slice 404, is located in the collection of 3-D data sets. User interface 400 may also include a projection image selector 412 to enable a user to select one of the original 2-D projection images. While not depicted, FIG. 400 may allow for volume rendering of a region of interest analogous to that of ROI rendering 310.

The invention claimed is:

1. A method for using computer-aided detection (CAD) algorithms to aid diagnosis and visualization of tomosynthesis mammography data, the method comprising:

processing tomosynthesis data with a CAD algorithm engine; and visualizing tomosynthesis data in a user-selected direction selected in a user interface from a plurality of visualization directions including directions corresponding to standard mammography views and directions not corresponding to standard mammography views.

2. The method of claim 1, further comprising:

inputting a tomosynthesis data set, wherein the data set includes a set of two-dimensional (2D) projection images and a three-dimensional (3D) reconstruction image;

segmenting breast tissue area on all of the set of 2D projection images to produce segmented breast tissue areas for each image of the set of 2D projection images;

detecting mass density candidates and microcalcification cluster candidates in the segmented breast tissue areas of each image of the set of 2D projection images;

back-projecting a set of locations oldie mass density candidates and microcalcification cluster candidates locations into the 3D reconstruction image from a limited number of angles;

merging the mass density candidates to compensate for errors due to the limited number of angles used for back-projection;

merging the microcalcification cluster candidates to compensate for errors due to the limited number of angles used for back-projection;

extracting a set of 3D mass density features and classifying each of the mass density candidates;

extracting a set of 3D microcalcification cluster features and classifying each of the microcalcification cluster candidates;

combining the classified mass density candidates and the classified microcalcification cluster candidates; and analyzing the combined candidates to provide detection and diagnosis information to a radiologist.

3. The method of claim 1, wherein the user interface to visualize tomosynthesis data includes:

at least one volume of 3D reconstructed tomosynthesis image data and at least one set of 2D projection images from a plurality of angles;

a volume rendering of a region of interest extracted from the 3D volume data;

a pointer user interface that is suited to define a region of interest; and a scrolling user interface that controls a direction of multiplanar reformatting or angle of projection.

4. The method of claim 3, wherein the direction of multiplanar reformatting includes any of the major axes of the at least one volume of 3D reconstructed tomosynthesis image data, or an arbitrary direction defined by using the pointer user interface to move a cube side selection icon.

5. The method of claim 3, wherein the angle of projection includes a selected 2D projection image from the at least one set of 2D projections, the selected 2D projection image being selected by using the pointer user interface to move an angle selection icon.

6. The method of claim 3, wherein the region of interest includes a 3D region selected by the pointer user interface.

7. The method of claim 3, wherein the volume rendering includes a rendered 2D projection of a 3D region of interest.

8. The method of claim 4, wherein the multiplanar reformatting is synchronized across multiple volumes.

9. The method of claim 5, wherein the one of the 2D projections is synchronized across multiple data sets.

10. A system using computer-aided detection (CAD) algorithms to aid diagnosis and visualization of tomosynthesis mammography data, the system comprising:

a CAD algorithm engine to process a set of tomosynthesis data, the set of tomosynthesis data comprising two-dimensional (2D) images, and three-dimensional (3D) image data; and a user interface to visualize the set of tomosynthesis data in a user-selected direction selected from a plurality of visualization directions including directions corresponding to standard mammography views and directions not corresponding to standard mammography views using multiplanar reformatting and volume rendering.

11. The system of claim 10, wherein the user interface provides a cuboidal interface icon.

12. The system of claim 11, wherein the cuboidal interface icon is configured to:

indicate a first location of a displayed 2D image slice in relation to the 3D image data from which the displayed 2D image slice is derived; and allow a user to select a new 2D image slice for display by selecting a second location which is associated with the new 2D image slice.

13. The system of claim 12, wherein the cuboidal interface icon is further configured to:

indicate a first orientation of the displayed 2D image slice in relation to the 3D image data; and allow a user to select the new 2D image slice for display by selecting a second orientation which is associated with the new 2D image slice.

14. The system of claim 10, wherein the user interface further comprises a dominant 2D image slice viewing field, the dominant 2D image slice viewing field depicting a cuboidal set of image data with a dominant surface displaying a 2D image slice obtained from the 3D image data.

15. The system of claim 14, wherein the dominant 2D image slice viewing field is further configured to display a superimposed 3D rendering of a portion of the displayed 2D image slice, the portion of the displayed 2D image slice being a limited area of the 2D image slice selected by a user.

* * * * *